US009949750B2

(12) United States Patent
Nguyen et al.

(10) Patent No.: US 9,949,750 B2
(45) Date of Patent: Apr. 24, 2018

(54) ROTATABLE MEDICAL DEVICE

(71) Applicant: Boston Scientific Scimed, Inc., Maple Grove, MN (US)

(72) Inventors: Man M. Nguyen, West Roxbury, MA (US); Gary S. Kappel, Acton, MA (US); Gerald R. Heller, Bedford, MA (US); Lawrence E. Stanton, Burlington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 15/463,563

(22) Filed: Mar. 20, 2017

(65) Prior Publication Data

US 2017/0189044 A1    Jul. 6, 2017

Related U.S. Application Data

(63) Continuation of application No. 13/664,722, filed on Oct. 31, 2012, now abandoned.

(60) Provisional application No. 61/553,467, filed on Oct. 31, 2011.

(51) Int. Cl.
| A61B 17/00 | (2006.01) |
| A61B 17/29 | (2006.01) |
| A61B 17/3205 | (2006.01) |

(52) U.S. Cl.
CPC .... *A61B 17/2909* (2013.01); *A61B 17/32056* (2013.01); *A61B 2017/0046* (2013.01); *A61B 2017/2929* (2013.01)

(58) Field of Classification Search
CPC .......... A61B 17/2909; A61B 17/32056; A61B 2017/0046; A61B 2017/2929

USPC ............................................................ 606/1
See application file for complete search history.

(56) References Cited

U.S. PATENT DOCUMENTS

| 3,955,578 A | 5/1976 | Chamness et al. |
| 4,977,900 A | 12/1990 | Fehling et al. |
| 5,066,295 A | 11/1991 | Kozak et al. |
| 5,084,054 A | 1/1992 | Bencini et al. |
| 5,114,403 A | 5/1992 | Clarke et al. |
| 5,158,561 A | 10/1992 | Rydell et al. |
| 5,183,470 A | 2/1993 | Wetterman |
| 5,201,743 A | 4/1993 | Haber et al. |

(Continued)

FOREIGN PATENT DOCUMENTS

| EP | 1 302 178 | 4/2003 |
| WO | WO 97/13455 | 4/1997 |

OTHER PUBLICATIONS

International Search Report and Written Opinion of PCT/US2012/062794, dated Feb. 1, 2013 (11 pages).

*Primary Examiner* — Aaron Roane
(74) *Attorney, Agent, or Firm* — Bookoff McAndrews, PLLC

(57) ABSTRACT

Medical devices and methods for using medical devices are disclosed. An example medical device may include a tubular member having a lumen defined therein and a proximal end. A shaft may extend through the lumen. The shaft may have a distal end and a proximal end. An end effector may be attached to the distal end of the shaft. A handle may be coupled to the proximal end of the tubular member. The handle may include a base, a first hub member attached to the base, a second hub member coupled to the first hub member, and a cap attached to the second hub member.

18 Claims, 9 Drawing Sheets

(56) References Cited

U.S. PATENT DOCUMENTS

| | | |
|---|---|---|
| 5,238,004 A | 8/1993 | Sahatjian et al. |
| 5,342,371 A * | 8/1994 | Welter .................. A61B 17/29 606/108 |
| 5,423,799 A | 6/1995 | Shiu |
| 5,439,005 A | 8/1995 | Vaughn |
| 5,573,530 A | 11/1996 | Fleury et al. |
| 5,676,542 A | 10/1997 | Lingenhöle et al. |
| 5,769,841 A | 6/1998 | Odell et al. |
| 5,772,609 A | 6/1998 | Nguyen et al. |
| 5,984,920 A | 11/1999 | Steinbach |
| 6,015,381 A | 1/2000 | Ouchi |
| 6,027,460 A | 2/2000 | Shturman |
| 6,074,408 A | 6/2000 | Freeman |
| 6,090,129 A | 7/2000 | Ouchi |
| 6,139,510 A | 10/2000 | Palermo |
| 6,423,054 B1 | 7/2002 | Ouchi |
| 6,443,909 B1 | 9/2002 | Ouchi |
| 6,508,803 B1 | 1/2003 | Horikawa et al. |
| 6,939,352 B2 | 9/2005 | Buzzard et al. |
| 7,476,244 B2 | 1/2009 | Buzzard et al. |
| 7,686,826 B2 | 3/2010 | Lee et al. |
| 2002/0095161 A1 | 7/2002 | Dhindsa |
| 2003/0074045 A1 | 4/2003 | Buzzard et al. |
| 2003/0167060 A1 | 9/2003 | Buzzard et al. |
| 2005/0107668 A1 | 5/2005 | Smith |
| 2005/0113845 A1 | 5/2005 | Griego et al. |
| 2006/0161190 A1 | 7/2006 | Gadberry et al. |
| 2006/0178658 A1 | 8/2006 | Smith |
| 2006/0189978 A1 | 8/2006 | Smith |
| 2006/0195104 A1* | 8/2006 | Schlafli .................. A61B 17/60 606/291 |
| 2007/0016161 A1* | 1/2007 | Costa .................... A61M 39/26 604/411 |
| 2007/0142844 A1 | 6/2007 | Kotmel et al. |
| 2009/0281375 A1 | 11/2009 | Sugita |
| 2010/0094087 A1 | 4/2010 | Hutchins et al. |
| 2010/0191278 A1 | 7/2010 | Lee et al. |

\* cited by examiner

ROTATABLE MEDICAL DEVICE

CROSS-REFERENCE TO RELATED APPLICATIONS

This application is a continuation of U.S. application Ser. No. 13/664,722, filed Oct. 31, 2012, which claims priority under 35 U.S.C. § 119 to U.S. Provisional Application No. 61/553,467, filed Oct. 31, 2011, all of which are incorporated herein by reference in their entireties.

TECHNICAL FIELD

The present disclosure pertains to medical devices, and methods for manufacturing medical devices. More particularly, the present disclosure pertains to elongated intracorporeal medical devices including a tubular member connected with other structures, and methods for manufacturing and using such devices.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

The invention provides design, material, manufacturing method, and use alternatives for medical devices. An example medical device may include a tubular member having a lumen defined therein and a proximal end. A shaft may extend through the lumen. The shaft may have a distal end and a proximal end. An end effector (e.g., a snare, needle, clevis, brush, tome, forceps, grasper, etc.) may be attached to the distal end of the shaft. A handle may be coupled to the proximal end of the tubular member. The handle may include a base, a first hub member attached to the base, a second hub member coupled to the first hub member, and a cap attached to the second hub member.

Another example medical device may include a tubular member having a lumen defined therein and a proximal end. A shaft may extend through the lumen. The shaft may have a distal end and a proximal end. An end effector may be attached to the distal end of the shaft. A handle assembly may be coupled to the proximal end of the tubular member. The handle assembly may include a rotation assembly. The rotation assembly may include and/or consist of a base, a first hub member attached to an outer surface of the base, a second hub member coupled to the first hub member and rotatable relative to the first hub member, and a cap threadably attached to the second hub.

Another example medical device may include a tubular member having a lumen defined therein and a proximal end. A shaft may extend through the lumen. The shaft may have a distal end and a proximal end. An end effector may be attached to the distal end of the shaft. A handle assembly may be coupled to the proximal end of the tubular member. The handle assembly may include a rotation assembly. The rotation assembly may include a monolithic base and first hub member, a second hub member coupled to the monolithic base and first hub member and rotatable relative to the monolithic base and the first hub member, and a cap threadably attached to the second hub.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
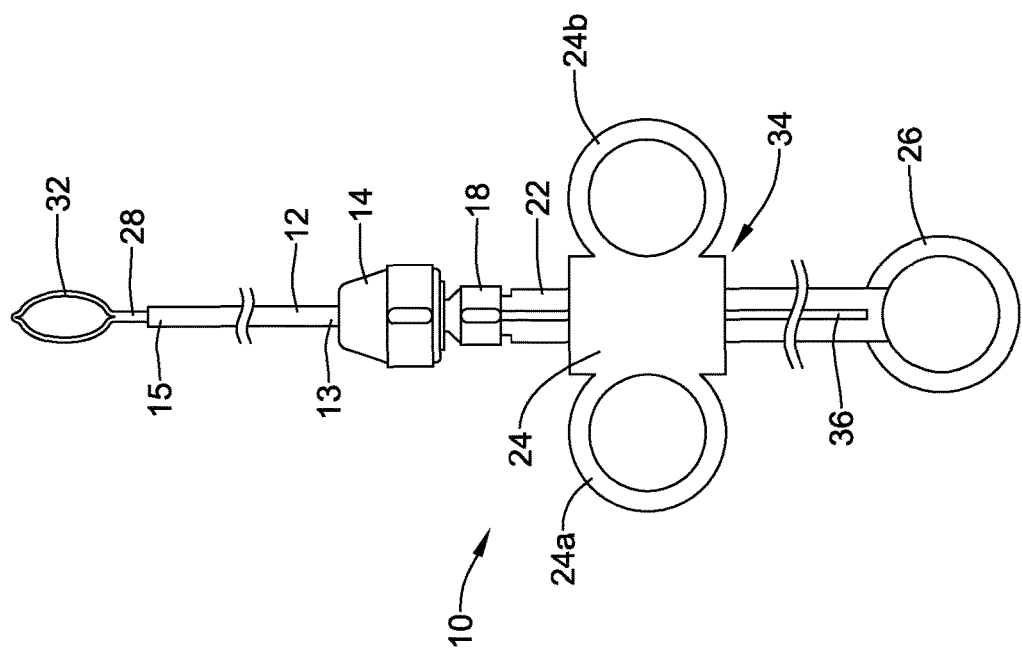
FIG. 1 is a side view of an example medical device.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 is a perspective view of an example medical device 10. Device 10 may include an elongate sheath 12. In general, sheath 12 may take the form of a polymer or metal tube. In some embodiments, sheath 12 may be constructed with a reinforcing braid, liner, web, weave, etc. Sheath 12 may include a proximal end region 13 and a distal end region 15. A handle assembly 34 may be coupled to proximal end region 13. A shaft 28 may be slidably disposed within at least a portion of sheath 12. Shaft 28 may take the form of a metal wire, a tube, a braid or braided wire, or the like. An end effector 32 may be coupled to the distal end region of shaft 28. End effector 32 may include a variety of possible structures and/or configurations. For example, end effector 32 may include a snare, needle, clevis, brush, tome, forceps, grasper, hemostatic clip, etc. These are just examples.

At handle assembly 34, a gripping member 24 may be coupled to a base member 22. In at least some embodiments, gripping member 24 may include finger rings 24a and 24b. Accordingly, a clinician may utilize finger rings 24a and 24b to move gripping member 24 so as to longitudinally shift the position of shaft 28 relative to sheath 12. For example, gripping member 24 may slide along base member 22 in order to shift shaft 28 between a first position, where end effector 32 is disposed within sheath 12, and a second position, where end effector 32 is disposed distally of sheath 12. Base member 22 may have a longitudinal slot 36 formed therein. Slot 36 may allow a portion 37 (not shown in FIG. 1 or 2, but can be seen in FIG. 3) of gripping member 24 to extend therethrough and attach to shaft 28. Portion 37 can move longitudinally through slot 36 when shaft 28 is shifted between the first and second configurations. A rotation member 26 may be coupled to a proximal end region of base member 22. Due to a connection between base member 22 (and/or gripping member 24) and shaft 28, rotation member 26 may be used to rotate shaft 28 and, thus, end effector 32.

Figure 2:
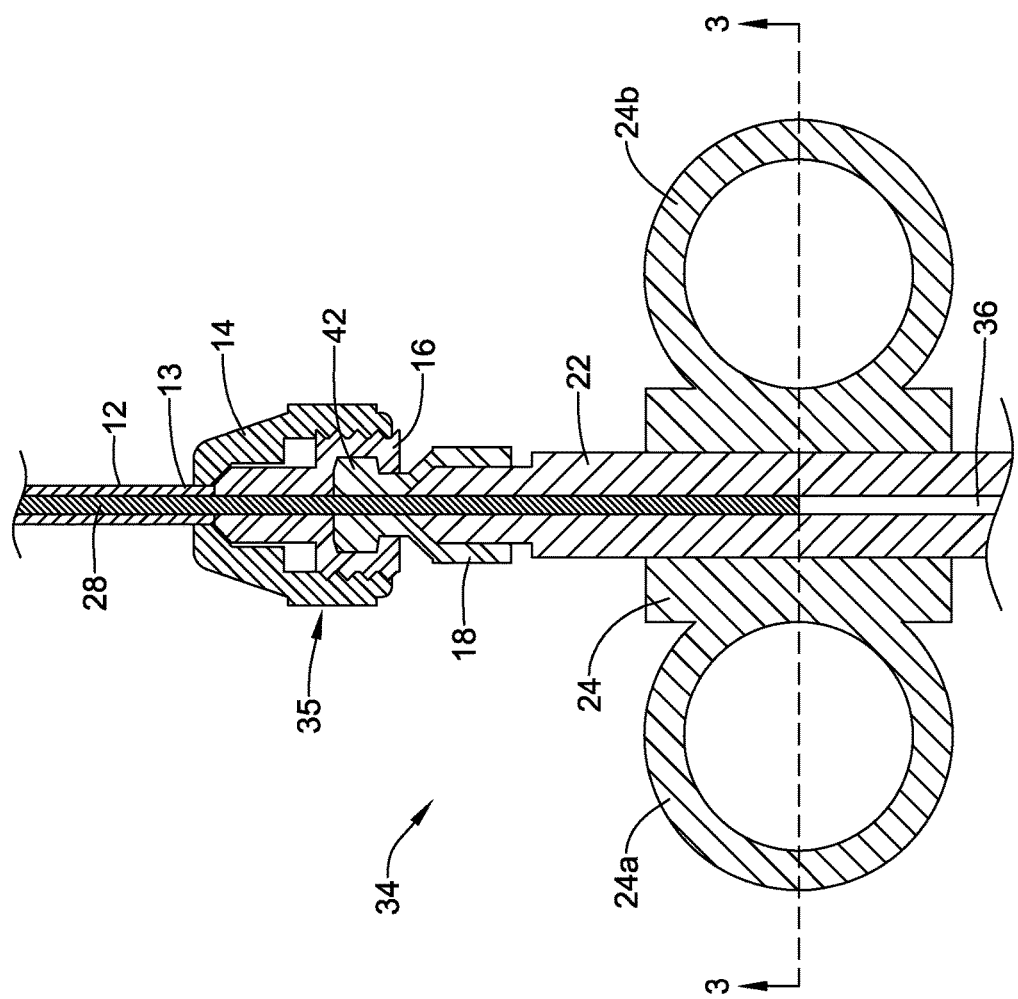
FIG. 2 is a cross-sectional view of a portion of the example medical device shown in FIG. 1.
Figure 3:
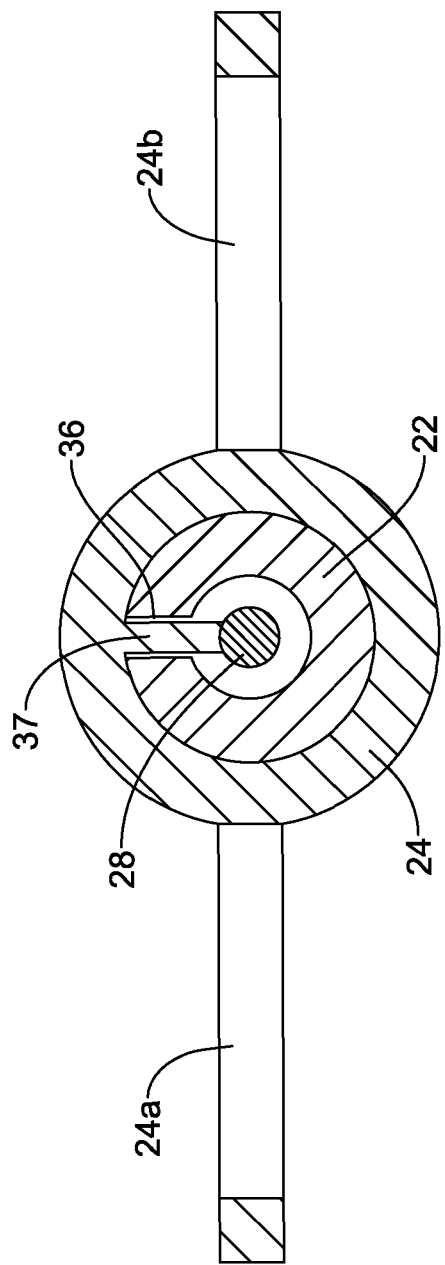
FIG. 3 is a transverse cross-sectional view of a portion of the example medical device along line 3-3.

Device 10 may be designed so that a user can easily guide end effector 32 to the intended target region within a body lumen. In addition, handle assembly 34 may be designed with relatively few components so as to simplify manufacturing and lower production cost. For example, handle assembly 34 may include a rotation assembly 35 that includes base member 22, a first hub member 18, a second hub member 16, and a cap 14 as shown in FIG. 2. In at least some embodiments, these components (base member 22, first hub member 18, second hub member 16, and cap 14) may be the only components of rotation assembly 35. Alternatively, device 10 may include additional features and/or components (e.g., different rotation assembly including those with more or fewer components than rotation assembly 35) that may allow a clinician to rotate shaft 28. For example, although FIG. 2 shows cap 14 and second hub member 16 as distinct components, it can be appreciated that in some embodiments cap 14 and second hub member 16 may be combined into a single, monolithic component. Similarly, in some of these and in other embodiments first hub member 18 and base member 22 may be combined into a single, monolithic component.

The connections between the components of handle assembly 34 and/or rotation assembly 35 may vary. For example, first hub member 18 may be attached to base member 22 along an outer surface of base member 22. In at least some embodiments, the bond or connection between first hub member 18 and base member 22 may be a substantially fixed and/or "non-rotatable" bond. The precise type of bond, however, may vary. For example, first hub member 18 may be attached to base member 22 with an adhesive bond, a thermal bond, a mechanical bond (e.g., a threaded connection), combinations thereof, or the like.

First hub member 18 may be coupled to second hub member 16. In general, the joint or connection between first hub member 18 and second hub member 16 may be a rotatable connection. Accordingly, second hub member 16 may be rotatable relative to or otherwise about first hub member 18. The form of the rotatable connection between first hub member 18 and second hub member 16 may vary. For example, first hub member 18 may include a projection or flange 42 formed at a distal end thereof. Second hub member 16 may have a cavity 38 formed therein. In embodiments with these features, flange 42 of first hub member 18 may be disposed within cavity 38 of second hub member 16. Additionally, the method of coupling first hub member 18 and second hub member 16 may vary. For example, second hub member 16 could "snap" onto first hub member 18. In addition, the rotatable connection between first hub member 18 and second hub member 16 may also be configured to be fluid tight. For example, a seal member or O-ring may be disposed at the rotatable connection of first hub member 18 and second hub member 16 to effect a fluid tight seal.

Cap 14 may be coupled to second hub member 16. The form of this connection may vary. For example, cap 14 may be bonded to second hub member 16 with a threaded connection. Alternatively, cap 14 could "snap" onto second hub member 16. However, any other suitable connection may be utilized without departing from the spirit of the invention.

Although the above example utilizes "threads" as the coupling interface between cap 14 and second hub member 16, a variety of coupling mechanisms may be contemplated without departing from the spirit of the invention. For example, cap 14 and second hub member 16 may be designed such that cap 14 "snaps" onto second hub member 16 and locks second hub member 16 onto flange 42, effectively eliminating independent rotation of second hub member 16 with first hub member 18.

In use, a clinician may advance medical device 10 through a body lumen to a position adjacent to an area of interest. For example, medical device 10 may be used to excise a polyp in the colon of a patient. While advancing medical device 10, end effector 32 may be disposed within the distal end of sheath 12. After advancing medical device 10 to the area of interest (i.e., near a polyp), the clinician may slide gripping member 24 from a proximal position to a distal position, thereby extending end effector 32 distally out of sheath 12. The clinician may then rotate end effector 32 in order to position end effector 32 substantially over the polyp. In order for the clinician to effectively manipulate end effector 32, the clinician may grasp cap 14 while rotating gripping member 24. The clinician may then slide gripping member 24 in a proximal direction, effectively tightening end effector 32 around the polyp. This tightening effect squeezes the polyp against the distal end of sheath 12, effectively severing the polyp. The clinician may then retract end effector 32 into the distal end of sheath 12 and remove medical device 10 from the body lumen.

Figure 4:
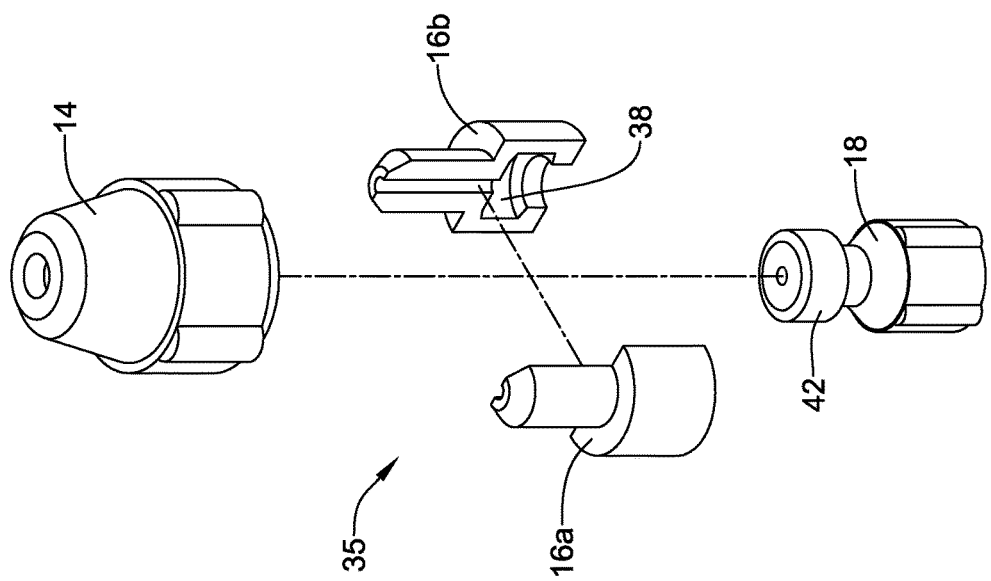
FIG. 4 is an exploded view of a portion of an example medical device.
Figure 5:
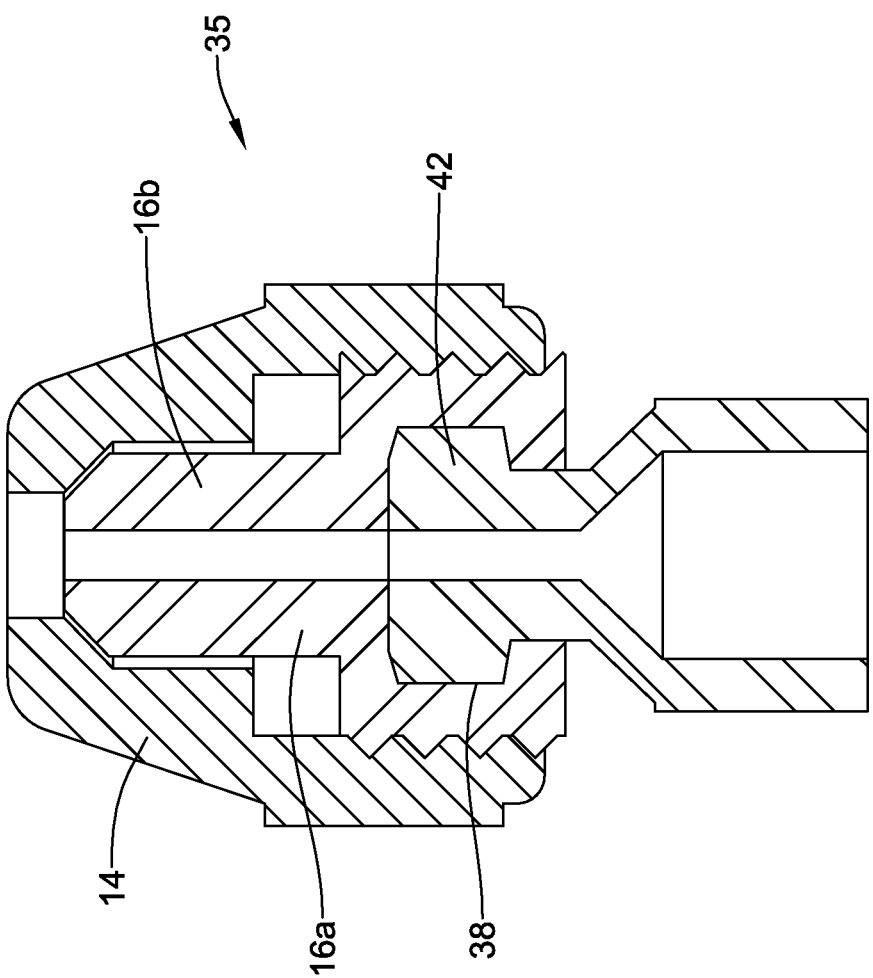
FIG. 5 is a cross-sectional view of a portion of the example medical device shown in FIG. 4.

In at least some embodiments, second hub member 16 may be constructed or otherwise include a pair of hub enclosures 16a/16b as shown in FIGS. 4-5. Hub enclosures 16a/16b, when attached, may define cavity 38 therein. To attach second hub member 16 to first hub member 18, enclosures 16a and 16b may connect together and be "around" flange 42. Cavity 38 of second hub member 16 may be sized to allow for clearance around flange 42. Clearance between flange 42 and the walls of cavity 38 may be generally configured to permit rotation between first hub member 18 and second hub member 16. It can be appreciated that the geometry of flange 42 and cavity 38 (or, more generally, the cross-sectional geometries of first hub member 18 and second hub member 16) may be designed a variety of ways while achieving the same functional result. For example, a ball/socket, flat disk/socket or cone/socket may be utilized.

Second hub member 16 may be coupled to cap 14 through a threaded connection. Accordingly, cap 14 generally does not rotate independently of second hub member 16. Instead, cap 14 and second hub member 16, together, may rotate relative to first hub member 18. Cap 14 and second hub member 16 may be held or otherwise remain stationary as first hub member 18 is rotated (e.g., by rotating base member 22). Because first hub member 18 may be coupled to base member 22, and base member 22 may be coupled to gripping member 24, rotation may occur by rotating base member 22 and/or gripping member 24 (and/or rotation member 26). In practice, a clinician may want to grasp cap 14 while rotating gripping member 24. Grasping cap 14 may allow the clinician to maintain control and stability of medical device 10 while still allowing positioning of end effector 32 through rotation and longitudinal manipulation of gripping member 24.

Figure 6:
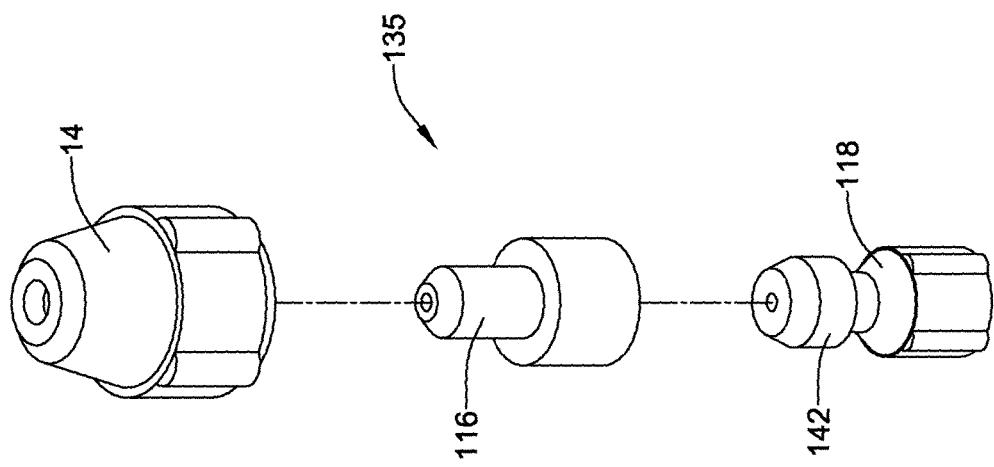
FIG. 6 is an exploded view of a portion of another example medical device.
Figure 7:
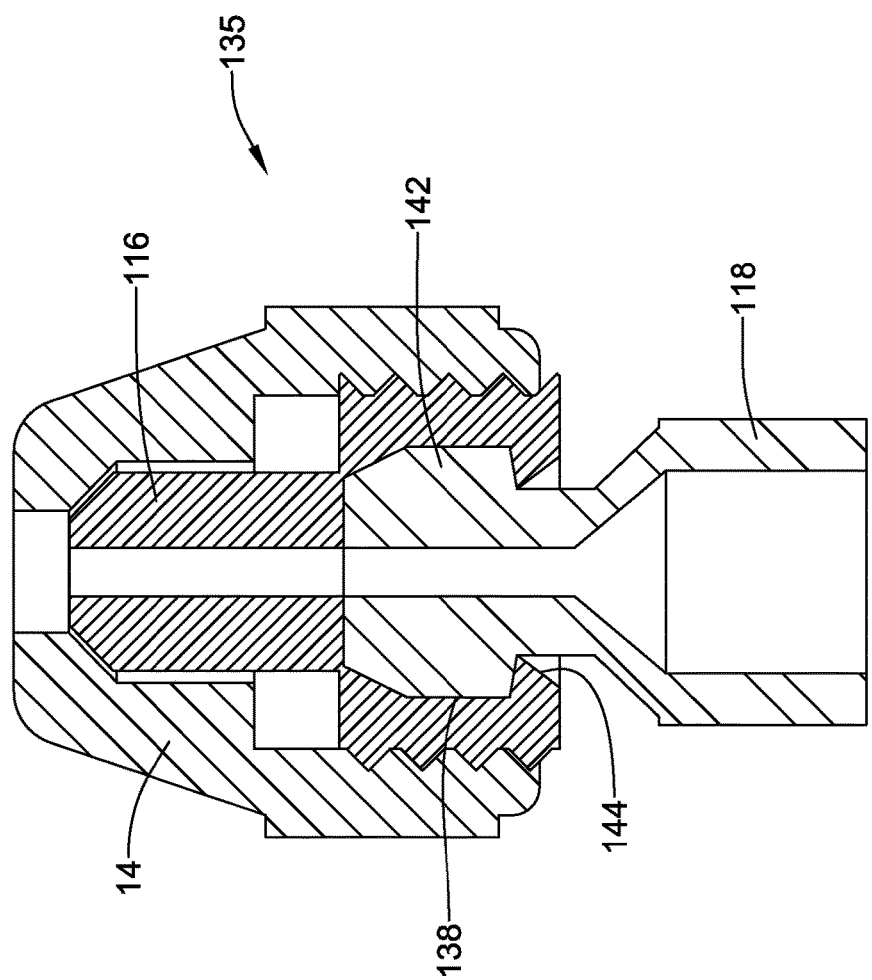
FIG. 7 is a cross-sectional view of a portion of the example medical device shown in FIG. 6.

FIGS. 6-7 show another example rotation assembly 135. In this embodiment, second hub member 116, rather than being formed of a pair of separate hub enclosures, may take the form of a molded hub that defines cavity 138 therein. A variety of manufacturing techniques may achieve this design. For example, second hub member 116 may be insert-molded over first hub member 118. Alternatively, second hub member 116 may include chamfer 144, for example located adjacent to a proximal opening of cavity 138. Accordingly, first hub member 118 may be designed to be "press-fit" into cavity 138 of second hub member 116. As such, chamfer 144 may allow flange 142 to more easily "snap" into cavity 138.

It is further contemplated that cap 14, in conjunction with second hub member 16 (and/or other second hub members disclosed herein), may be configured to limit the free rotation of second hub member 16 with respect to first hub member 18. This may be achieved by configuring cap 14 to compress second hub member 16 when cap 14 is screwed onto to second hub member 16. For example, cap 14 may be formed as or otherwise resemble a collet. Thus, as cap 14 is threaded down onto second hub member 16, cap 14 may exert a radially inward force onto second hub member 16. This may compress or otherwise deform second hub member 16 such that second hub member 16 is compressed onto or about first hub member 18 (e.g., compressed onto flange 42 of first hub member 18). It is contemplated that cap 14 may be threaded onto second hub member 16 so that rotation of second hub member 16 relative to first hub member 18 is reduced. It is further contemplated that cap 14 may be threaded onto second hub member 16 so that rotation of second hub member 16 relative to first hub member 18 is substantially prevented altogether (e.g., second hub member 16 may be "locked" relative to second hub member 16).

Figure 8:
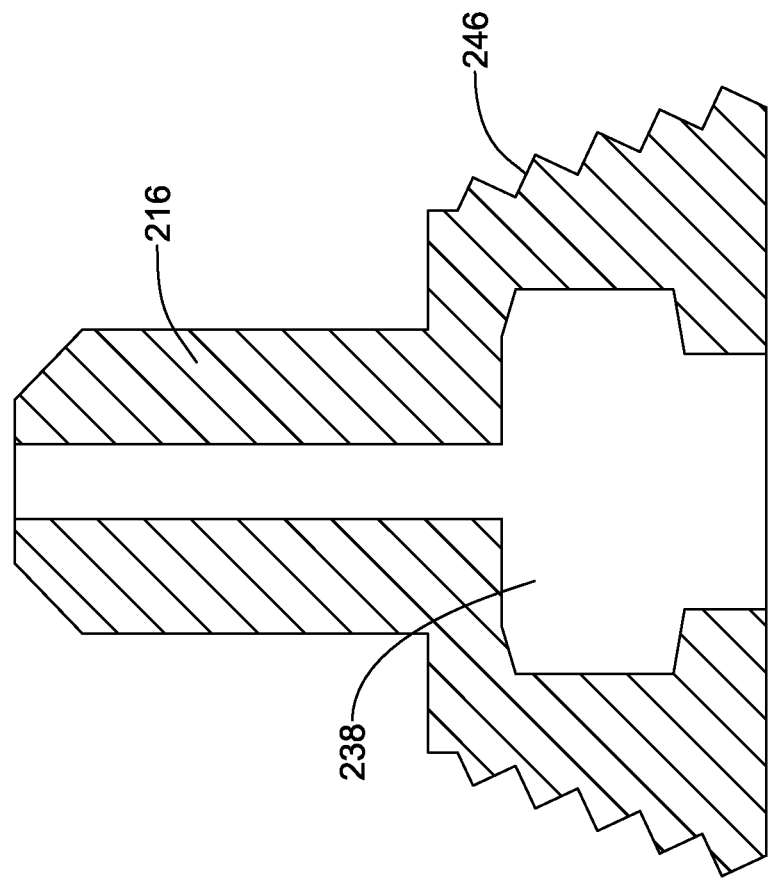
FIG. 8 is a cross-sectional view of a portion of another example medical device.

Cap 14 and second hub member 16 may be configured in multiple ways to achieve this result. For example, as shown in FIG. 8, threads 246 of second hub member 216 may be tapered such that when cap 14 is screwed onto second hub member 216, second hub member 216 flexes or otherwise deflects radially inward. The inward flexing of second hub member 216 may result in a reduction in the diameter of cavity 238. It can be appreciated that the degree to which cap 14 travels along threads 246 may control the amount of inward flex of second hub member 216. As a result, the user can control the degree to which second hub member 216 compresses onto first hub member 18. The range may be from no compression to that which will be sufficient to "lock" second hub member 216 onto first hub member 18 (e.g., elimination of independent rotation of second hub member 16 with first hub member 18).

Figure 9:
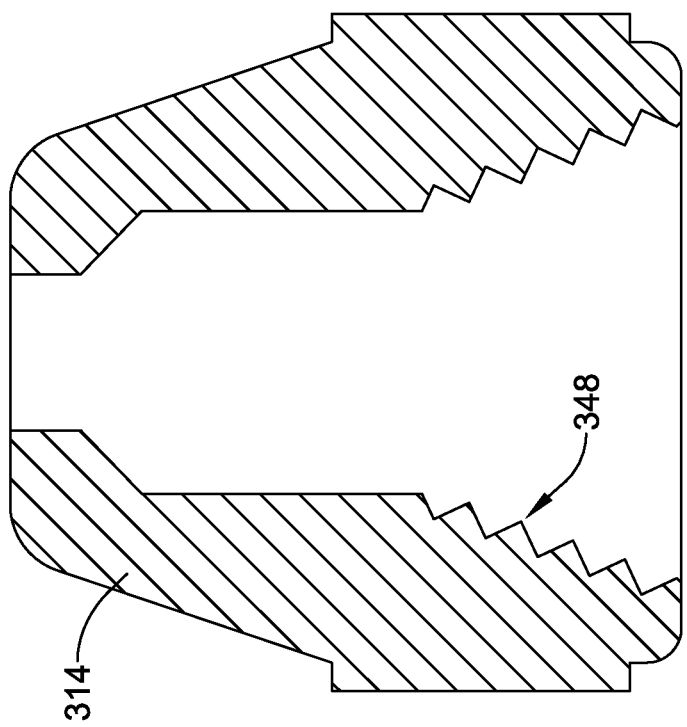
FIG. 9 is a cross-sectional view of a portion of another example medical device.

In a reciprocal fashion, as shown in FIG. 9, threads 348 of cap 314 may be tapered such that when cap 314 is screwed onto second hub member 16, second hub member flexes inward. The inward flexing of second hub member 16 results in a reduction in the diameter of cavity 38. It can be appreciated that the degree to which cap 314 travels along threads 348 controls the amount of inward flex of second hub member 16. As a result, the user can control the degree to which second hub member 16 compresses onto first hub member 18. The range may be from no compression to that which will be sufficient to "lock" second hub member 16 onto first hub member 18 (e.g., elimination of independent rotation of second hub member 16 with first hub member 18).

The materials that can be used for the various components of device 10 (and/or other devices disclosed herein) and the various components thereof disclosed herein may include those commonly associated with medical devices. For simplicity purposes, the following discussion makes reference to sheath 12 and other components of device 10. However, this is not intended to limit the devices and methods described herein, as the discussion may be applied to other similar tubular members and/or components of tubular members or devices disclosed herein.

Sheath 12 and/or other components of device 10 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of sheath 12 and/or other components of device 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of device 10 to achieve the same result.

In some embodiments, a degree of Magnetic Resonance Imaging (MRI) compatibility is imparted into device 10. For example, sheath 12, or portions thereof, may be made of a material that does not substantially distort the image and create substantial artifacts (i.e., gaps in the image). Certain ferromagnetic materials, for example, may not be suitable because they may create artifacts in an MRI image. Sheath 12, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the exterior surface of the device 10 (including, for example, the exterior surface of sheath 12) may include a coating, for example a lubricious, a hydrophilic, a protective, or other type of coating. Hydrophobic coatings such as fluoropolymers provide a dry lubricity which improves guidewire handling and device exchanges. Suitable lubricious polymers may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical device, comprising:
   a tubular member having a lumen defined therein, a distal end, and a proximal end;
   a shaft extending through the lumen, the shaft having a distal end and a proximal end;
   an end effector at the distal end of the shaft; and
   a handle coupled to the proximal end of the tubular member, wherein the handle includes:
     a base,
     a first hub member coupled to the base, such that the first hub member and the base move unitarily,
     a second hub member coupled to the first hub member, such that the first hub member is received within the second hub member, and
     a cap coupled to the second hub member, such that the second hub member and the first hub member both extend into a chamber within the cap,
   wherein a portion of the shaft is received in the base, such that the portion of the shaft is slidable distally relative to the base to extend the end effector distally from the distal end of the tubular member.

2. The medical device of claim 1, wherein the second hub member comprises a first enclosure member and a second enclosure member, wherein the first enclosure member and the second enclosure member are discrete, wherein a surface of the first enclosure member and a surface of the second enclosure member are held in abutting contact by the cap, and wherein the surface of the first enclosure member and the surface of the second enclosure member are opposing surfaces that face each other.

3. The medical device of claim 1, wherein the chamber is configured to receive an enlarged distal end of the first hub member.

4. The medical device of claim 3, wherein the second hub member is configured to rotate relative to the first hub member.

5. The medical device of claim 1, wherein the second hub member is coupled to the cap with a threaded connection.

6. The medical device of claim 1, wherein the second hub member is configured to exert a compressive force onto the first hub member to inhibit relative rotation between the second hub member and the first hub member via frictional engagement between the second hub member and the first hub member.

7. The medical device of claim 1, wherein the second hub member is coupled to the first hub member with a snap-fit connection.

8. The medical device of claim 1, wherein the first hub member is coupled to the base with a threaded connection.

9. The medical device of claim 1, wherein the base has a slot formed therein for slidably receiving the portion of the shaft, and wherein a gripping member is disposed along the base, the gripping member having a projection that extends into the slot and attaches to the portion of the shaft.

10. The medical device of claim 9, wherein the gripping member is slidable along the base.

11. The medical device of claim 1, wherein the first hub member is fixedly coupled to a radially outward facing surface of the base.

12. The medical device of claim 1, wherein the cap includes a tapering threaded interior surface.

13. The medical device of claim 12, wherein the second hub member includes a tapering threaded exterior surface.

14. The medical device of claim 13, wherein the tapering threaded interior surface engages the tapering threaded exterior surface to couple the cap to the second hub member.

15. A medical device comprising:
    a tubular member having a lumen defined therein, a distal end, and a proximal end;
    a shaft extending through the lumen, the shaft having a distal end and a proximal end;
    an end effector at the distal end of the shaft; and
    a handle assembly coupled to the proximal end of the tubular member, the handle assembly including a rotation assembly, the rotation assembly including:
      a base,
      a first hub member coupled to an outer surface of the base,
      a second hub member coupled to the first hub member such that the first hub member is received within the second hub member and the second hub member is rotatable relative to the first hub member, wherein:
        the second hub member includes a first portion having a surface, and a second portion having a surface, the surfaces of the first and second portions being configured to move into abutting contact with each other, and
      a cap coupled to the second hub member such that the second hub member is received within the cap, wherein the cap is configured to hold the surfaces of the first and second portions in abutting contact with each other, and wherein the second hub member, the cap, and the tubular member are coupled to rotate unitarily, and
    wherein a portion of the shaft is received in the base, and the portion of the shaft is longitudinally slidable relative to the base.

16. The medical device of claim 15, wherein the second hub member has a chamber formed therein, and wherein the chamber is configured to receive a projection of the first hub member.

17. The medical device of claim 16, wherein the second hub member is configured to rotate relative to the first hub member about the projection.

18. The medical device of claim 15, wherein the shaft extends through the base, the base has slot formed therein, and a gripping member is disposed along the base and has a projection that extends through the slot and is attached to the shaft.

* * * * *